(12) United States Patent
Kobayashi et al.

(10) Patent No.: US 10,993,799 B2
(45) Date of Patent: May 4, 2021

(54) INTRAOCULAR LENS INSERTION SYSTEM, INTRAOCULAR LENS INSERTION APPARATUS, AND TUBE

(71) Applicant: KOWA COMPANY, LTD., Nagoya (JP)

(72) Inventors: Kenichi Kobayashi, Nagoya (JP); Shuji Abe, Nagoya (JP); Genyo Midorikawa, Nagoya (JP)

(73) Assignee: KOWA COMPANY, LTD., Nagoya (JP)

( * ) Notice: Subject to any disclaimer, the term of this patent is extended or adjusted under 35 U.S.C. 154(b) by 274 days.

(21) Appl. No.: 15/768,741

(22) PCT Filed: Sep. 28, 2016

(86) PCT No.: PCT/JP2016/078630
§ 371 (c)(1),
(2) Date: Apr. 16, 2018

(87) PCT Pub. No.: WO2017/065007
PCT Pub. Date: Apr. 20, 2017

(65) Prior Publication Data
US 2018/0296321 A1 Oct. 18, 2018

(30) Foreign Application Priority Data

Oct. 16, 2015 (JP) .............................. JP2015-204896

(51) Int. Cl.
*A61F 2/16* (2006.01)
*A61F 9/007* (2006.01)
*A61B 17/00* (2006.01)

(52) U.S. Cl.
CPC ................ *A61F 2/167* (2013.01); *A61F 2/16* (2013.01); *A61F 2/1662* (2013.01);
(Continued)

(58) Field of Classification Search
CPC .......... A61F 2/16; A61F 2/1662; A61F 2/167; A61F 2/1672; A61F 2/1675; A61F 9/007; A61F 2/1691; A61B 2017/00398
See application file for complete search history.

(56) References Cited

U.S. PATENT DOCUMENTS

| | | |
|---|---|---|
| 2007/0168026 A1 | 7/2007 | Nagasaka |
| 2007/0270945 A1 | 11/2007 | Kobayashi et al. |

(Continued)

FOREIGN PATENT DOCUMENTS

| | | |
|---|---|---|
| CA | 2797245 A1 | 10/2011 |
| JP | 2007 185255 A | 7/2007 |

(Continued)

OTHER PUBLICATIONS

Extended European Search Report issued in corresponding European Patent Application No. 16855261.0 dated May 24, 2019.

*Primary Examiner* — George J Ulsh
(74) *Attorney, Agent, or Firm* — Knobbe, Martens, Olson & Bear LLP

(57) ABSTRACT

It is provided an intraocular lens insertion system that achieves a preferable insertion of an intraocular lens without using viscoelastic material in an eyeball. The intraocular lens insertion system includes an intraocular lens insertion apparatus configured to use a predetermined driving force to move an intraocular lens and insert the intraocular lens into an eyeball, an irrigating solution infusion apparatus configured to infuse irrigating solution into the eyeball, a driving source configured to deliver the predetermined driving force to the intraocular lens insertion apparatus, an irrigating solution source configured to deliver the irrigating solution to the irrigating solution infusion apparatus, and a switching unit configured to switch in a multistage manner a control of a delivery of the irrigating solution from the irrigating solution source to the irrigating solution infusion apparatus (Continued)

and a control of a delivery of the predetermined driving force from the driving source to the intraocular lens insertion apparatus.

12 Claims, 7 Drawing Sheets

(52) U.S. Cl.
CPC .......... *A61F 2/1672* (2013.01); *A61F 2/1675* (2013.01); *A61F 9/007* (2013.01); *A61B 2017/00398* (2013.01); *A61F 2/1691* (2013.01)

(56) References Cited

U.S. PATENT DOCUMENTS

| | | |
|---|---|---|
| 2008/0027460 A1 | 1/2008 | Kobayashi |
| 2008/0071286 A1 | 3/2008 | Kobayashi et al. |
| 2010/0076450 A1 | 3/2010 | Yoshida et al. |
| 2010/0094309 A1 | 4/2010 | Boukhny et al. |
| 2010/0256652 A1 | 10/2010 | Kobayashi et al. |
| 2011/0172676 A1 | 7/2011 | Chen |
| 2011/0264102 A1* | 10/2011 | Cole .................... A61F 2/1662 606/107 |
| 2013/0197531 A1 | 8/2013 | Boukhny et al. |
| 2014/0200590 A1 | 7/2014 | Chen |

FOREIGN PATENT DOCUMENTS

| | | |
|---|---|---|
| JP | 2007 190360 A | 8/2007 |
| JP | 2007 330783 A | 12/2007 |
| JP | 2009 240729 A | 10/2009 |
| JP | 2010 063777 A | 3/2010 |
| JP | 2012 505066 A | 3/2012 |
| JP | 2014 050484 A | 3/2014 |
| WO | WO 2008/149927 A1 | 12/2008 |
| WO | WO 2011/133853 A1 | 10/2011 |
| WO | WO 2014/193953 A2 | 12/2014 |
| WO | WO 2015/144890 A1 | 10/2015 |

* cited by examiner

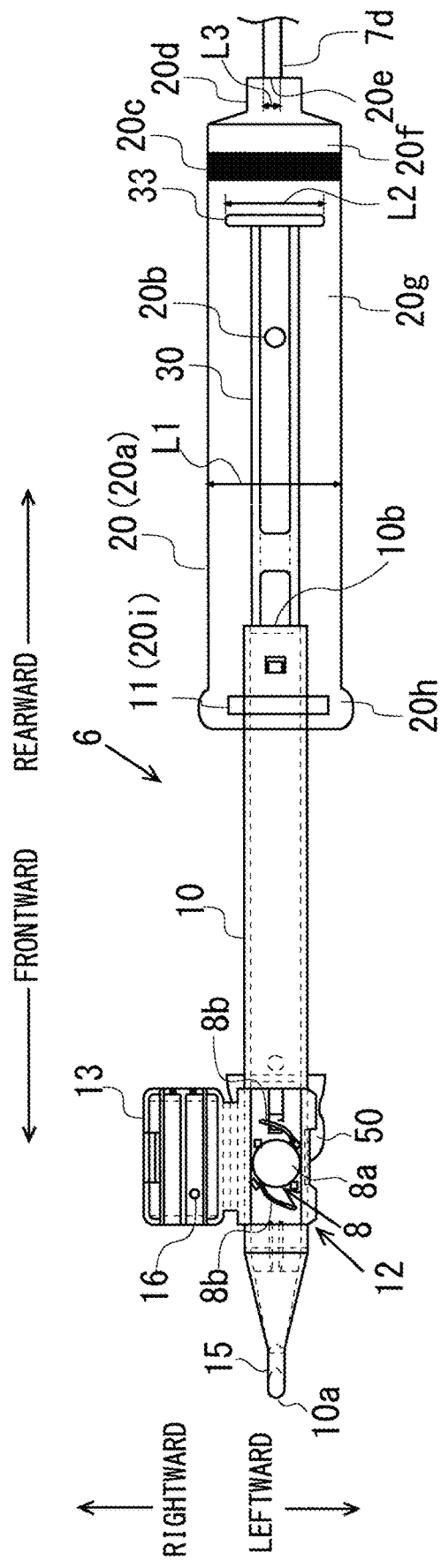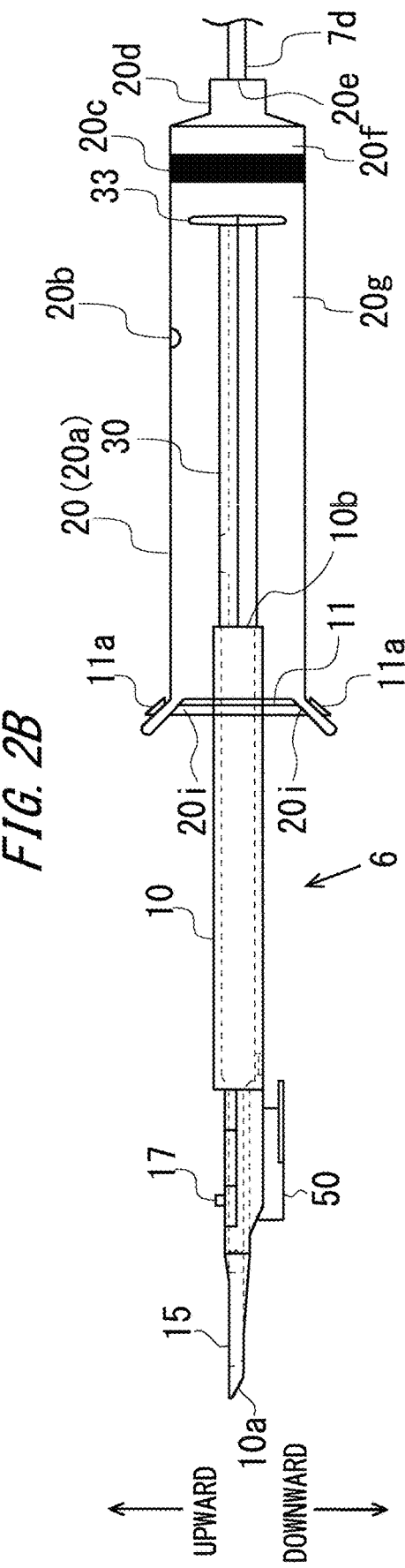

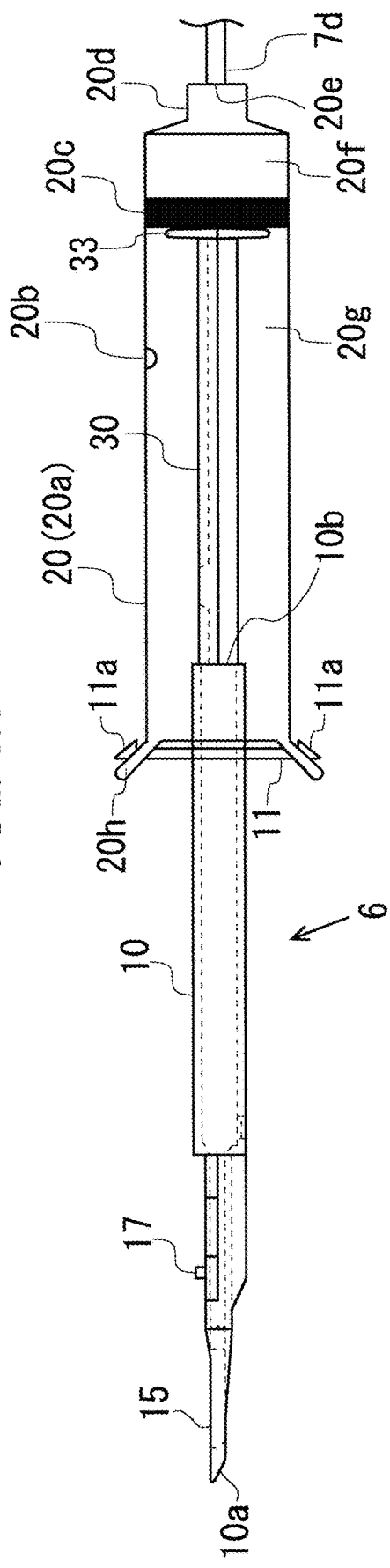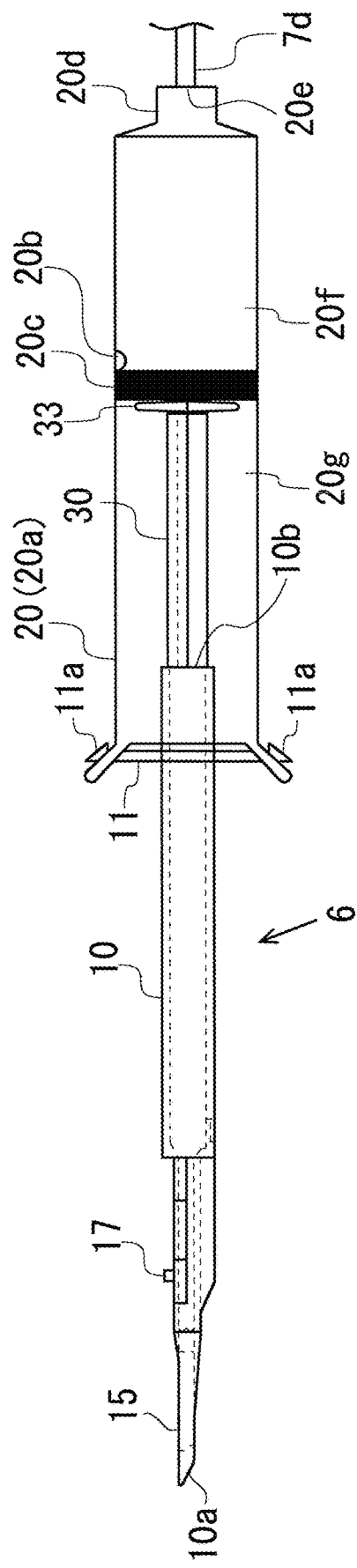

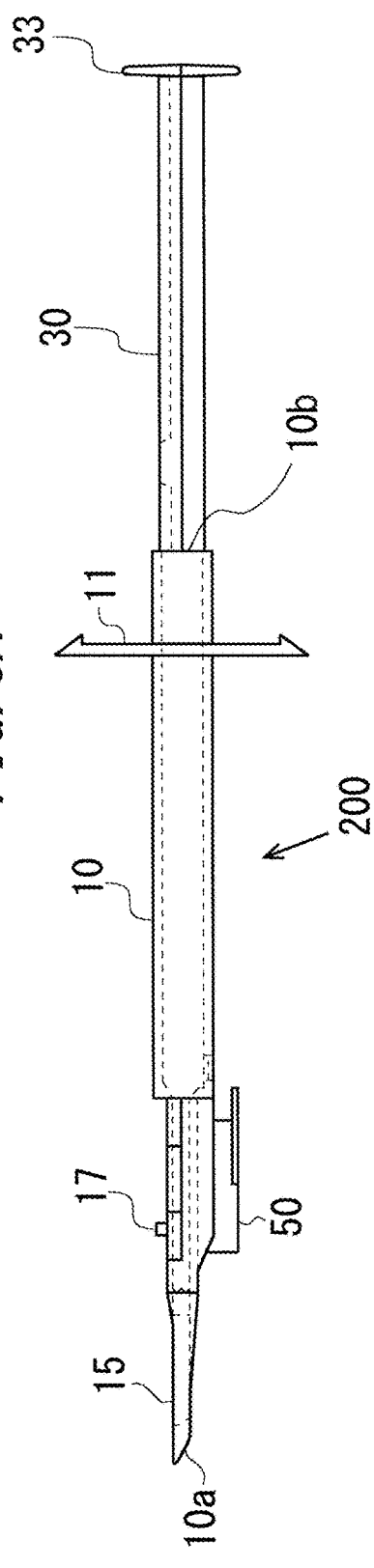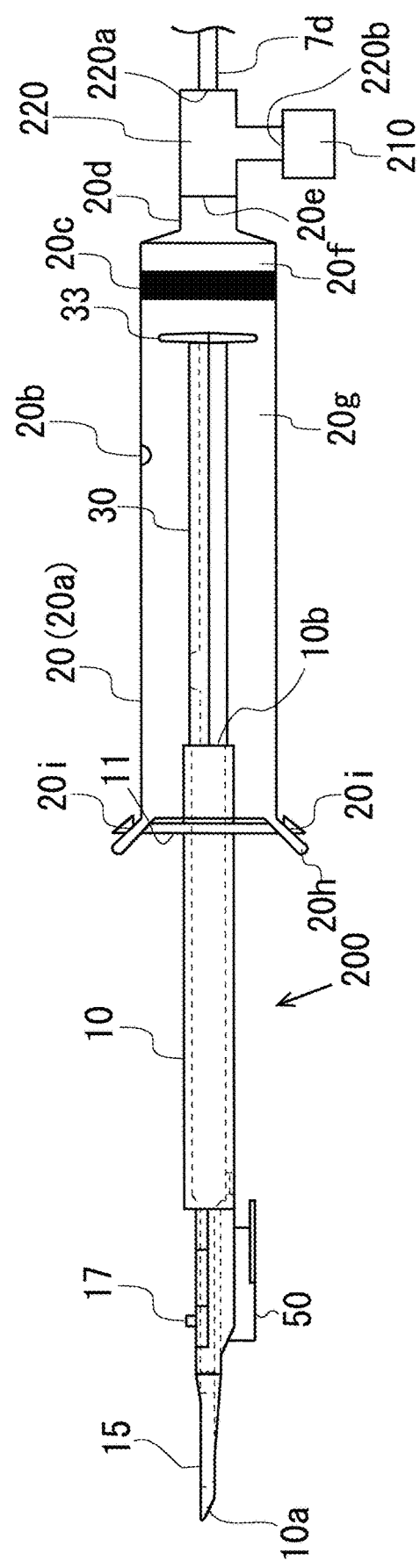

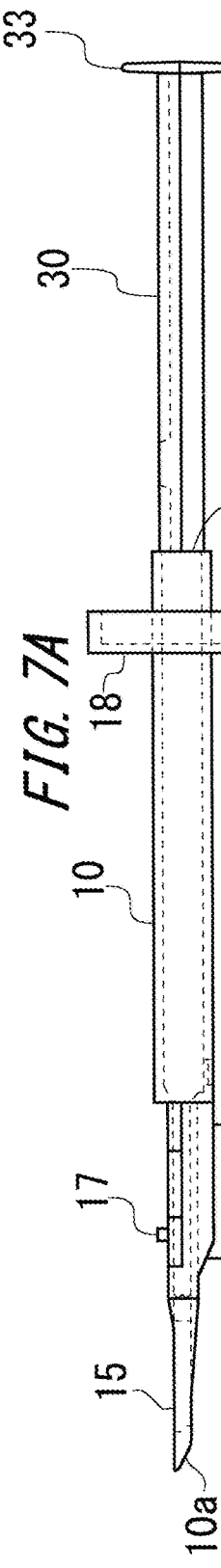
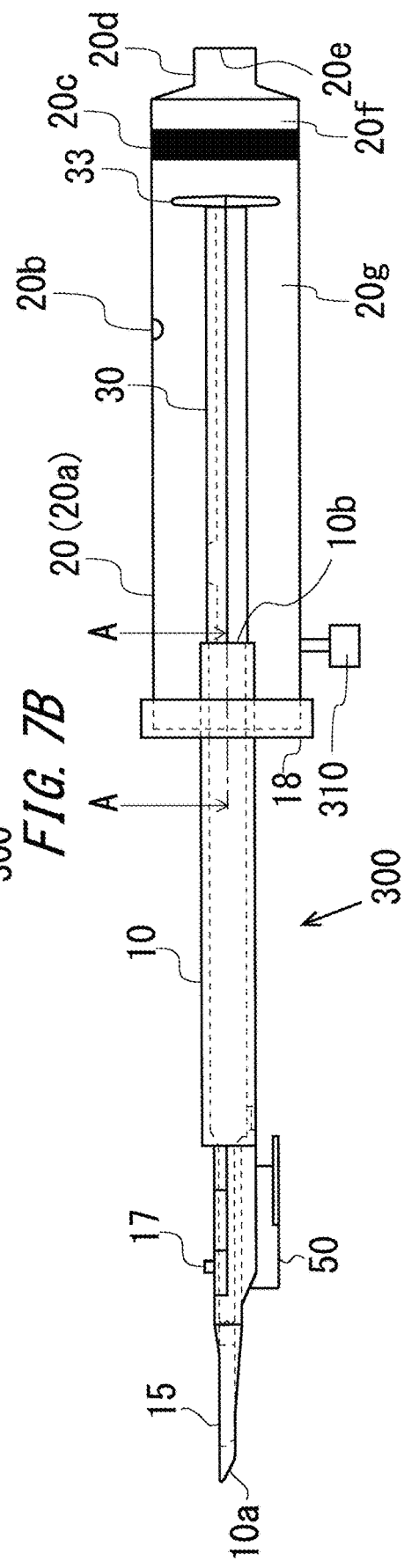
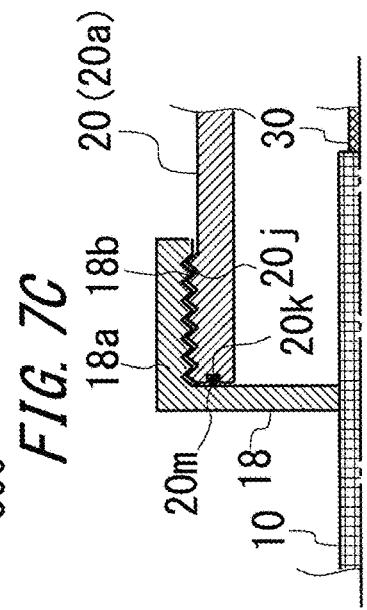

INTRAOCULAR LENS INSERTION SYSTEM, INTRAOCULAR LENS INSERTION APPARATUS, AND TUBE

FIELD

The embodiments discussed herein relate to an intraocular lens insertion system, an intraocular lens insertion apparatus and a tube.

BACKGROUND

Intraocular lenses are widely used to be replaced with human opacity crystalline lenses in cataract treatments to compensate the optical powers of the lenses. In intraocular lens insertion surgeries for the cataract treatments, an incision (discission cut) which is several millimeters in length is produced at the edge of the cornea or the sclerocornea, the human crystalline lens is crushed and removed by phacoemulsification and aspiration etc. and what is called viscoelastic material is infused into the capsule of crystalline lens and the capsule is dilated. Next, an intraocular lens insertion apparatus is used to inject an intraocular lens into the eyeball and to arrange the position of the intraocular lens in the eyeball. When the arrangement of the position of the intraocular lens is completed, the infused viscoelastic material is removed from the eyeball.

Recently, techniques for assisting the insertion of an intraocular lens into an eyeball of a patient by using an intraocular lens insertion apparatus are proposed (See Patent Literatures 1-4). In these techniques, balanced salt solution (BSS) is used instead of viscoelastic material as irrigating solution to dilate the capsule of crystalline lens after the phacoemulsification and aspiration is performed. The irrigating solution is delivered into the capsule via a fluid path formed in the intraocular lens insertion apparatus. Then, the intraocular lens is inserted into the eyeball and the position of the intraocular lens in the eyeball is arranged while the anterior chamber is dilated by the irrigating solution delivered into the capsule. In addition, an intraocular lens insertion apparatus for automatically inserting an intraocular lens into an eyeball is also proposed (See Patent Literature 5, for example).

CITATION LIST

Patent Literature

[PTL 1] JP-A-2007-190360
[PTL 2] JP-A-2007-330783
[PTL 3] JP-A-2010-63777
[PTL 4] WO 2008/149927
[PTL 5] JP-T-2012-505066

SUMMARY

Technical Problem

In a conventional intraocular lens insertion apparatus, the irrigating solution delivered into the intraocular lens insertion apparatus also flows into a path on which the intraocular lens moves. As a result, lubricant attached to the inner wall forming the path on which the intraocular lens moves in the intraocular lens insertion apparatus may be removed by the irrigating solution continuously flowing through the path. Therefore, the movement of the intraocular lens in the intraocular lens insertion apparatus may be affected by this event.

The technique of this disclosure has been made in view of the above-mentioned circumstances, and it is an object of this disclosure to provide an intraocular lens insertion system for providing irrigating solution into an eyeball and facilitating a preferable insertion of an intraocular lens into the eyeball.

Solution to Problem

According to the embodiments described herein, it is provided intraocular lens insertion system including an intraocular lens insertion apparatus configured to use a predetermined driving force to move an intraocular lens and insert the intraocular lens into an eyeball, an irrigating solution infusion apparatus configured to infuse irrigating solution into the eyeball, a driving source configured to deliver the predetermined driving force to the intraocular lens insertion apparatus, an irrigating solution source configured to deliver the irrigating solution to the irrigating solution infusion apparatus, and a switching unit configured to switch in a multistage manner a control of a delivery of the irrigating solution from the irrigating solution source to the irrigating solution infusion apparatus and a control of a delivery of the predetermined driving force from the driving source to the intraocular lens insertion apparatus.

With such a configuration, since irrigating solution can be delivered via a path other than a path for inserting the intraocular lens into the eyeball, a concern such that lubricant may be removed in the path for moving the intraocular lens in the intraocular lens insertion apparatus and this may affect the movement of the intraocular lens can be resolved. In addition, the user can perform the infusion of irrigating solution into the eyeball and the insertion of the intraocular lens as a series of operations. Since the operation of delivering the irrigating solution into the eyeball and the operation of inserting the intraocular lens into the eyeball are independent in conventional intraocular lens insertion systems, the user performs each operation separately. However, the user can use the switching unit of the intraocular lens insertion system according to the present embodiment to perform these operations as a series of operations.

In addition, the above intraocular lens insertion system can be configured so that the switching unit is configured to switch in the multistage manner the control of the delivery of the irrigating solution from the irrigating solution source to the irrigating solution infusion apparatus and the control of a combination of the control of the delivery of the irrigating solution from the irrigating solution source to the irrigating solution infusion apparatus and the control of the delivery of the predetermined driving force from the driving source to the intraocular lens insertion apparatus. With such a configuration, the user can maintain the delivery of the irrigating solution into the eyeball while the user is performing the operation of inserting the intraocular lens into the eyeball. Further, the switching unit can be configured to connect with each of the intraocular lens insertion apparatus, the irrigating solution infusion apparatus, the driving source and the irrigating solution source. Moreover, the switching unit can be configured to connect directly with the driving source and the irrigating solution source. Additionally, the switching unit can be configured to be a foot pedal.

In addition, the intraocular lens insertion system can be configured to further include a control unit configured to control the delivery of the irrigating solution to the irrigating solution infusion apparatus according to an operation of the foot pedal. Additionally, the intraocular lens insertion system can be configured to further include a control unit configured to control the delivery of the predetermined driving force to the intraocular lens insertion apparatus according to an operation of the foot pedal. Further, the intraocular lens insertion system can be configured such that the cross section of the irrigating solution providing unit of the irrigating solution infusion apparatus is smaller than the cross section of the nozzle member of the intraocular lens insertion apparatus. Moreover, the intraocular lens insertion system can be configured such that the inner wall forming the path on which the intraocular lens moves in the intraocular lens insertion apparatus is wet in advance before the delivery of the driving force from the driving source to the intraocular lens insertion apparatus is started.

In addition, the intraocular lens insertion apparatus used in the intraocular lens insertion system can be configured such that the nozzle body is provided for the tip of the intraocular lens insertion apparatus, the intraocular lens is moved in the nozzle body by the driving force, and when the intraocular lens insertion apparatus is placed horizontally, a height of a distal end member of the nozzle body is equal to or more than 10 mm. Further, the intraocular lens insertion system can be configured such that the intraocular lens is housed in advance in the intraocular lens housing unit of the intraocular lens insertion apparatus. Moreover, it is provided a tube that is used in the above intraocular lens insertion system and that is configured to connect the switching unit with at least one of the intraocular lens insertion apparatus, the irrigating solution infusion apparatus, the driving source and the irrigating solution source.

Advantageous Effects of Invention

According to the technique disclosed herein, it is possible to provide an intraocular lens insertion system for facilitating a preferable insertion of an intraocular lens into an eyeball without infusing viscoelastic material into the eyeball.

BRIEF DESCRIPTION OF DRAWINGS

FIG. 2A is a diagram schematically illustrating a configuration of an intraocular lens insertion apparatus according to one embodiment.

FIG. 2B is another diagram schematically illustrating a configuration of an intraocular lens insertion apparatus according to one embodiment.

FIG. 5A is a diagram schematically illustrating an example of a movement of a plunger of an intraocular lens insertion apparatus according to one embodiment.

FIG. 5B is another diagram schematically illustrating an example of a movement of a plunger of an intraocular lens insertion apparatus according to one embodiment.

FIG. 6A is a diagram schematically illustrating a configuration of an intraocular lens insertion apparatus according to one embodiment.

FIG. 6B is another diagram schematically illustrating a configuration of an intraocular lens insertion apparatus according to one embodiment.

FIG. 7A is a diagram schematically illustrating a configuration of an intraocular lens insertion apparatus according to one embodiment.

FIG. 7B is another diagram schematically illustrating a configuration of an intraocular lens insertion apparatus according to one embodiment.

FIG. 7C is yet another diagram schematically illustrating a configuration of an intraocular lens insertion apparatus according to one embodiment.

DETAILED DESCRIPTION OF THE PREFERRED EMBODIMENT

Hereinafter, embodiments of the present invention are described with reference to drawings.

Figure 1A:
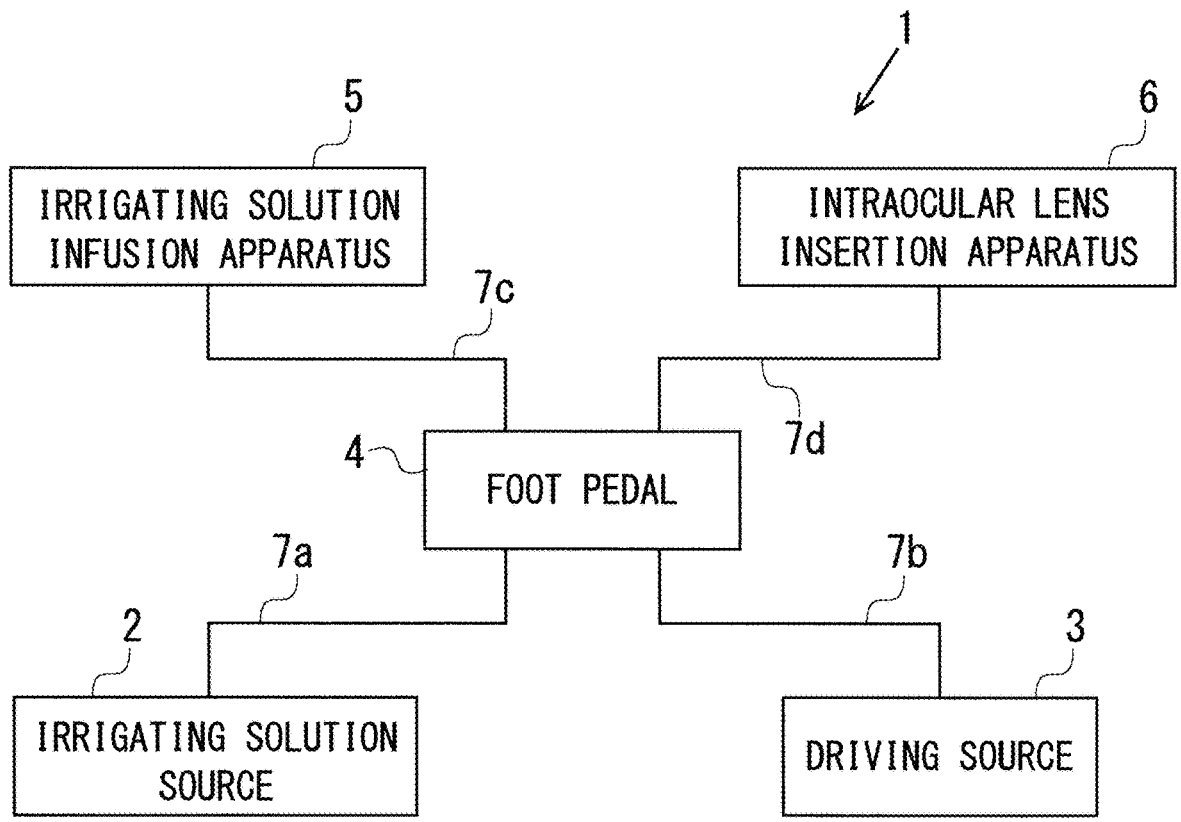
FIG. 1A is a diagram schematically illustrating a configuration of an intraocular lens insertion system according to one embodiment.
Figure 1B:
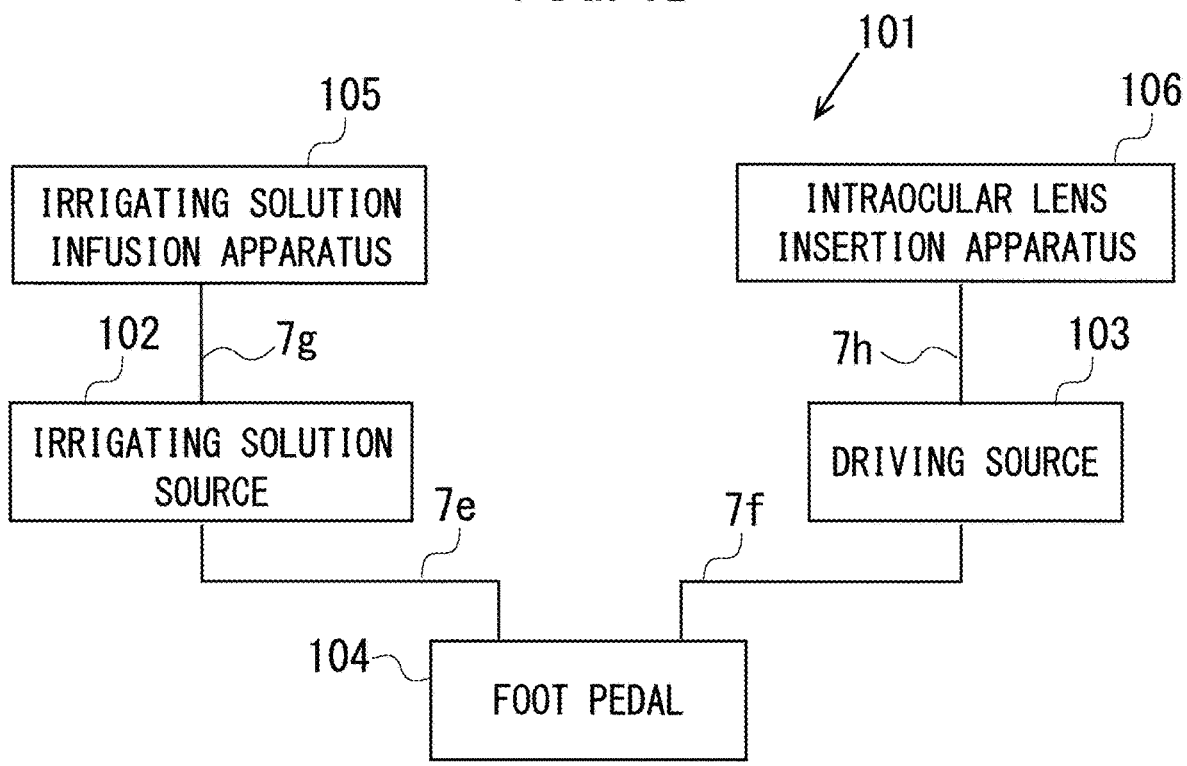
FIG. 1B is a diagram schematically illustrating a variation thereof.

FIG. 1 schematically illustrates a configuration of an intraocular lens insertion system 1 and an intraocular lens insertion system 101 according to the present embodiment. As illustrated in FIG. 1A, the intraocular lens insertion system 1 includes an irrigating solution source 2, a driving source 3, a foot pedal 4, an irrigating solution infusion apparatus 5 and an intraocular lens insertion apparatus 6. In addition, the irrigating solution source 2, the driving source 3, the foot pedal 4, the irrigating solution infusion apparatus 5 and the intraocular lens insertion apparatus 6 are connected with the foot pedal 4 via a tube 7a, a tube 7b, a tube 7c and a tube 7d, respectively. On the other hand, the intraocular lens insertion system 101 as illustrated in FIG. 1B is provided as a variation of the intraocular lens insertion system 1, and the intraocular lens insertion system 101 includes an irrigating solution source 102, a driving source 103, a foot pedal 104, an irrigating solution infusion apparatus 105 and an intraocular lens insertion apparatus 106. In addition, the irrigating solution source 102 and irrigating solution infusion apparatus 105 are connected with each other via a tube 7g, and the driving source 103 and the intraocular lens insertion apparatus 106 are connected with each other via a tube 7h. Further, the irrigating solution source 102 and the driving source 103 are electrically connected with the foot pedal 104 via a tube (electrical cable) 7e and a tube (electrical cable) 7f, respectively, which have a function of transmitting electrical signals.

In the intraocular lens insertion system 1, the irrigating solution infusion apparatus 5 is an apparatus for infusing irrigating solution delivered via the foot pedal 4 from the irrigating solution source 2 into an eyeball of a patient. BSS is an example of the irrigating solution. A medicament can be mixed with BSS expecting an effect of preventing an endophthalmitis. In addition, the intraocular lens insertion apparatus 6 is an apparatus for using the fluid delivered via the foot pedal 4 from the driving source 3 to insert an intraocular lens set in the intraocular lens insertion apparatus 6 into the eyeball. Air can be used as the fluid. A user operates the foot pedal 4 to control the delivery of the irrigating solution from the irrigating solution source 2 to the irrigating solution infusion apparatus 5 and the delivery of the driving force from the driving source 3 to the intraocular lens insertion apparatus 6.

On the other hand, the irrigating solution infusion apparatus 105 of the intraocular lens insertion system 101 is an apparatus for infusing irrigating solution delivered from the irrigating solution source 102 into the eyeball. In addition, the intraocular lens insertion apparatus 106 is an apparatus for using the fluid delivered from the driving source 103 to insert the intraocular lens set in the intraocular lens insertion apparatus 106 into the eyeball. The foot pedal 104 is connected with the irrigating solution source 102 and the driving source 103. The user operates the foot pedal 104 to control the irrigating solution source 102 and the driving source 103 to achieve control of the delivery of irrigating solution to the irrigating solution infusion apparatus 105 and control of the delivery of driving force from the driving source 103 to the intraocular lens insertion apparatus 106.

Although the foot pedals 4 and 104 are examples of a switching unit, the configuration of the switching unit is not limited to such a specific configuration as long as irrigating solution from the irrigating solution sources 2 and 102 can be delivered to the irrigating solution infusion apparatuses 5 and 105 and driving force from the driving sources 3 and 103 can be delivered to the intraocular lens insertion apparatuses 6 and 106.

Functions occurred in the intraocular lens insertion system 1 are described below. The foot pedal 4 switches the functions of the intraocular lens insertion system 1 according to the amount of thrust applied onto the pedal by the user. Specifically, when the user pedals the foot pedal 4 to the first position, the foot pedal 4 starts the delivery of irrigating solution from the irrigating solution source 2 to the irrigating solution infusion apparatus 5. In addition, when the user further pedals the foot pedal 4 from the first position to the second position, the foot pedal 4 starts the delivery of driving force from the driving source 3 to the intraocular lens insertion apparatus 6 in addition to the delivery of irrigating solution.

In conventional operations, a helper is in charge of infusing viscoelastic material into the intraocular lens insertion apparatus and arranging the intraocular lens in a standby position for insertion. However, according to the present embodiment, since the intraocular lens can be inserted smoothly after the anterior chamber is formed and maintained by irrigating solution, the user can complete the operation of the insertion of the intraocular lens on the user's own. In addition, when the user uses the foot pedal 4 to infuse irrigating solution into the eyeball and insert the intraocular lens into the eyeball on the user's own, there is a concern that the intraocular lens can be left at the standby position for insertion for a long time while the user uses irrigating solution to form and maintain the anterior chamber. However, since the formation and maintenance of the anterior chamber can be completed before the intraocular lens is arranged in the standby position for insertion as described above, the intraocular lens can be smoothly inserted into the eyeball without being left at the position for a long time.

When the foot pedal 4 is moved to a position shallower than the first position after the foot pedal is moved to the first position, the foot pedal 4 stops the delivery of irrigating solution from the irrigating solution source 2 to the irrigating solution infusion apparatus 5. Similarly, when the foot pedal 4 is moved to a position shallower than the second position after the user moves the foot pedal 4 to the second position, the foot pedal 4 stops the delivery of driving force from the driving source 3 to the intraocular lens insertion apparatus 6. When the position of the foot pedal 4 is deeper than the first position, the foot pedal 4 continues the delivery of irrigating solution from the irrigating solution source 2 to the irrigating solution infusion apparatus 5. Further, when the user moves the foot pedal 4 to a position deeper than the second position, the foot pedal 4 continues the delivery of driving force from the driving source 3 to the intraocular lens insertion apparatus 6 in addition to continuing the delivery of irrigating solution.

FIG. 2 schematically illustrates a configuration of the intraocular lens insertion apparatus 6 according to the present embodiment. FIG. 2A illustrates a plan view of the intraocular lens insertion apparatus 6 in a state where a stage lid member 13 is opened. FIG. 2B illustrates a side view of the intraocular lens insertion apparatus 6 in a state where the stage lid member 13 is closed. The intraocular lens insertion apparatus 6 includes a nozzle body 10, a plunger 30 as a pushing member for pushing an intraocular lens, an apparatus body which includes a stage member 12 and the stage lid member 13 as an accommodating member for accommodating an intraocular lens and can be used stand-alone to push the intraocular lens, and an intraocular lens push assisting apparatus 20 for assisting pushing of the intraocular lens. The stage member 12 is integrally or independently formed on the nozzle body 10. The plunger 30 is inserted into the nozzle body 10. An intraocular lens 8 is set on the stage member 12. The stage member 12 is integrally formed with the stage lid member 13. The intraocular lens push assisting apparatus 20 is a hollow cylindrical member and one end of the intraocular lens push assisting apparatus 20 is connected with a hold member 11 of the nozzle body 10. The shape of the intraocular lens push assisting apparatus 20 is not limited to the hollow cylindrical shape and the intraocular lens push assisting apparatus 20 can be formed into any shape.

When the intraocular lens 8 is pushed, viscoelastic material is injected for lubricate the intraocular lens insertion apparatus, generally. However, since BSS having a viscosity lower than the viscoelastic material is used in the present embodiment, it is possible that when the intraocular lens insertion apparatus 6 is laid on an operating table, BSS drains from the apparatus due to the inclination of the apparatus and the intraocular lens can be stuck when the intraocular lens is pushed. In addition, when the intraocular lens insertion apparatus 6 rolls on the table, it is possible that BSS drains from the apparatus due to the inclination of the apparatus. Therefore, the rolling of the intraocular lens insertion apparatus 6 when laid on a surface can be prevented during the operations by configuring the bottom surface of the intraocular lens insertion apparatus 6 to be a flat surface without protrusions or weighing the bottom of the intraocular lens insertion apparatus 6 etc. to keep the horizontal posture of the intraocular lens insertion apparatus 6.

Further, when the intraocular lens insertion apparatus 6 which is ready for use is laid on the operating table, BSS may drain from the apparatus because the nozzle distal end member 10a comes into contact with a surgical instrument such as tweezers. Therefore, such a drain of BSS can be prevented by adjusting the diameter of the intraocular lens push assisting apparatus 20 to arrange the nozzle distal end member 10a at a position above the operating table. Since the height above the operating table of the tweezers etc. used for eye surgery which are laid on the table generally ranges from 10 mm to 15 mm, it is desirable to arrange the height above a horizontal plane of the nozzle distal end member 10a which is laid on the plane to be more than 10 mm. It is more preferable to arrange the height to be about 20 mm.

With this arrangement, the inside diameter of the intraocular lens push assisting apparatus 20 is configured to be about ϕ30 mm.

The nozzle body 10 of the intraocular lens insertion apparatus 6 is formed in a tubular shape the cross section of which is a rectangle. An opening is formed at one end of the nozzle body 10 (which is referred to as a rear end member 10b). A nozzle member 15 and the distal end member 10a are formed in a tapering manner at the other end of the nozzle body 10. As illustrated in FIG. 2B, the opening of the distal end member 10a is formed into a bevel. The plunger 30 is inserted into the nozzle body 10 and can be moved to-and-fro in the nozzle body 10.

In the descriptions hereinafter, the direction extending toward the distal end member 10a from the rear end member 10b of the nozzle body 10 is assumed as the frontward direction, the direction opposite to the frontward direction is assumed as the rearward direction, the direction toward a viewer's side with respect to a paper surface on which FIG. 2 is drawn is assumed as the upward direction, the direction opposite to the upward direction is assumed as the downward direction, the direction toward a viewer's side with respect to a paper surface on which FIG. 2B is drawn is assumed as the leftward direction, and the direction opposite to the leftward direction is assumed as the rightward direction. In this case, the upward direction corresponds to a direction toward a front side along an optical axis of a lens body 8a described later, the downward direction corresponds to a direction toward a rear side along the optical axis of the lens body 8a, the frontward direction corresponds to a direction toward a front side in the pushing direction of the plunger 30, and the rearward direction corresponds to a direction toward a rear side in the pushing direction of the plunger 30.

A hold member 11 which projects in a plate shape and on which a user hooks the user's fingers when the user pushes the plunger 30 toward the distal end side of the nozzle body 10 is integrally formed on the nozzle body 10 in the vicinity of the rear end member 10b of the nozzle body 10. In addition, the stage member 12 on which the intraocular lens 8 is to be set is formed on the rear end side of the nozzle member 15 of the nozzle body 10. The stage member 12 is configured such that an upper side of the nozzle body 10 is opened by opening the stage lid member 13. Further, the positioning member 50 is mounted on the stage member 12 from below the nozzle body 10. With the use of the positioning member 50, the intraocular lens 8 is stably held on the stage member 12 even before the insertion apparatus 6 is used (during transportation).

That is, in the intraocular lens insertion apparatus 6, at the time of manufacturing the intraocular lens insertion apparatus 6, the intraocular lens 8 is set on the stage member 12 such that a front side along an optical axis is directed upward in a state where the stage lid member 13 is opened and the positioning member 50 is mounted on the stage member 12. Then, the intraocular lens insertion apparatus 6 is commercially distributed with the stage lid member 13 closed, and the intraocular lens insertion apparatus 6 is sold. Then, the user removes the positioning member 50 while holding the stage lid member 13 in a closed state and, thereafter, pushes the plunger 30 toward the distal end side of the nozzle body 10. Due to such an operation, the intraocular lens 8 is pushed by the plunger 30, and the intraocular lens 8 is ejected into the inside of the eyeball from the distal end member 10a. In the intraocular lens insertion apparatus 6, the nozzle body 10, the plunger 30 and the positioning member 50 are formed using a resin such as polypropylene. Polypropylene has been proven as a material used for medical apparatuses. In addition, polypropylene is reliable in chemical resistance etc. Further, although it is assumed in the present embodiment that the intraocular lens insertion apparatus 6 is preset-type such that the intraocular lens 8 is set in the intraocular lens insertion apparatus 6 in advance before its commercially distribution, a separate-type intraocular lens insertion apparatus such that the user manually sets the intraocular lens 8 in the intraocular lens insertion apparatus 6 before the surgery can be used instead of the preset-type intraocular lens insertion apparatus.

The intraocular lens push assisting apparatus 20 includes a cylindrical tube member 20a extending along the direction toward which the plunger 30 inserted into the nozzle body 10 extends. In addition, a through-hole 20b which penetrates the tube member 20a is formed on the side of the tube member 20a. Further, a piston 20c is provided as a move member on the rear end side of the tube member 20a. The piston 20c is configured to come into contact with the inner wall of the tube member 20a. Additionally, the piston 20c is configured to slide along the inner wall of the tube member 20a with maintaining the contact with the inner wall of the tube member 20a. It is desirable that the piston 20c has a rigidity so as not to bend during the slide along the inner wall. Moreover, a fluid delivery member 20d is provided as a fluid delivery means for delivering fluid to the space enclosed by the intraocular lens push assisting apparatus 20 and the piston 20c on the rear end side of the intraocular lens push assisting apparatus 20.

In addition, the space enclosed by the tube member 20a, the piston 20c and the fluid delivery member 20d is a closed space. It is noted in the present embodiment that an area on the side of the fluid delivery member 20d for the piston 20c as the boundary of the closed space is referred to as a first area 20f, and an area on the side of the plunger 30 inserted into the nozzle body 10 for the piston 20c as the boundary is referred to as a second area 20g. Further, the through-hole 20b has a function to drain the fluid delivered into the first area 20f to the outside of the intraocular lens push assisting apparatus 20.

An engaging member 20h for engaging with the hold member 11 of the nozzle body 10 is provided on the distal end side of the intraocular lens push assisting apparatus 20. As illustrated in FIG. 2B since the hold member 11 of the nozzle body 10 extends toward the upward direction and the downward direction, the engaging members 20h are provided in pairs for the intraocular lens push assisting apparatus 20 in the upward direction and the downward direction in the state where the intraocular lens push assisting apparatus 20 is attached to the nozzle body 10. In addition, a through-hole 20i penetrated by a part of the hold member 11 is provided for each engaging member 20h.

When the intraocular lens push assisting apparatus 20 is attached to the nozzle body 10, each end of the hold member 11 of the nozzle body 10 are inserted through the corresponding through-hole 20i of the engaging member 20h. And a notch 11a is provided for each end of the hold member 11. Therefore, once the engaging member 20h of the intraocular lens push assisting apparatus 20 is engaged with the hold member 11, the notch 11a prevents the engagement between the engaging member 20h and the hold member 11 from being released. The notch 11a can be formed on the engaging member 20h instead of the hold member 11 or on the engaging member 20h in addition to the hold member 11, as long as the engagement between the engaging member 20h and the hold member 11 is not released. When the intraocular lens push assisting apparatus 20 is attached to the nozzle body 10, at least one opening portion is needed to be provided for the intraocular lens push assisting apparatus 20 or the nozzle body at the connection point between the intraocular lens push assisting apparatus 20 and the nozzle body 10. The opening portion prevents the second area 20g from becoming a closed space. A reason for providing the opening portion is that air exists in the second area 20g before the intraocular lens push assisting apparatus 20 is attached to the nozzle body 10 is needed to be drained to the outside of the intraocular lens push assisting apparatus 20 according to the movement of the piston 20c.

An opening 20e for allowing the flow of the fluid delivered from the tube 7d is provided for the end surface of the fluid delivery member 20d on the rear end side thereof. The distal end portion of the fluid delivery member 20d is connected with the rear end portion of the tube member 20a, and the rear end portion of the fluid delivery member 20d can be connected with the distal end portion of the tube 7d. The inside diameter L1 of the tube member 20a is configured to be larger than the outside diameter L2 of the push plate member 33 of the plunger 30. On the other hand, the opening diameter L3 of the opening 20e of the fluid delivery member 20d is configured to be smaller than the inside diameter L1 of the tube member 20a.

The larger the size of the inside diameter L1 are, the larger thrust for the pushing becomes. This is because when fluid is delivered to the opening 20e with a constant pressure, the thrust F calculated according to the Pascal's law is proportional to the pressure receiving area A of the piston ($F[N]=A[mm^2] \times P[MPa]$). In an example in the present embodiment in which the supply air pressure P of the delivered fluid is about 0.1 MPa, desirable thrust F can be achieved by configuring the inside diameter L1 to be more than or equal to $\phi 15$ mm. In addition, it is desirable to configure the inside diameter L1 to be about $\phi 30$ mm given that the apparatus is handled by a hand of the user. Further, the size of the opening 20e is configured such that the opening 20e engages with the inner surface or the outer surface of the tube 7d. the opening 20e can be configured to connect with the tube 7d via a connector. In addition, the foot pedal 4 is connected with the other end of the tube 7d connected with the fluid delivery member 20d.

Figure 3A:
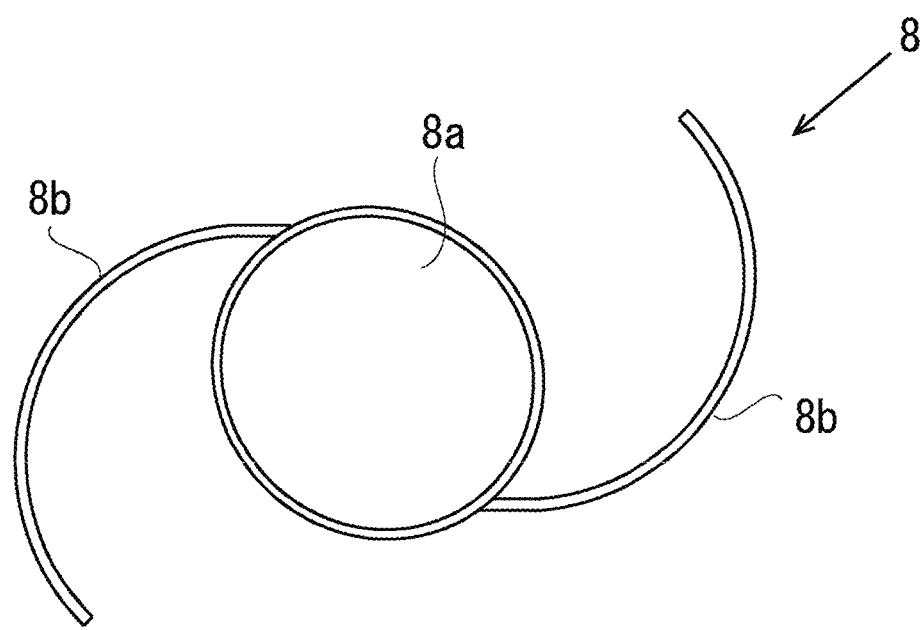
FIG. 3A is a diagram schematically illustrating a configuration of an intraocular lens according to one embodiment.
Figure 3B:
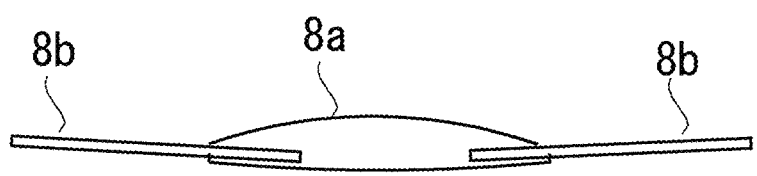
FIG. 3B is another diagram schematically illustrating a configuration of an intraocular lens according to one embodiment.

FIG. 3 is a diagram schematically illustrating the configuration of the intraocular lens 8. FIG. 3A is a diagram illustrating a plan view, and FIG. 3B is a diagram illustrating a side view. The intraocular lens 8 is what is called a three-piece type intraocular lens. The intraocular lens 8 is formed of the lens body 8a having a predetermined refractivity, and two hair-like support members 8b, 8b which are connected to the lens body 8a and are provided for holding the lens body 8a inside of the eyeball. The lens body 8a and the support members 8b are made from flexible resin materials. In the present embodiment, the intraocular lens 8 is set in the intraocular lens insertion apparatus 6 so that one of the support members 8b, 8b is arranged on the rear side of the intraocular lens 8 and the other of the support members 8b, 8b is arranged on the front side of the intraocular lens 8. Although it is assumed in the following descriptions that the intraocular lens 8 is a three-piece type intraocular lens, the descriptions can be applied to what is called a one-piece type intraocular lens in which the lens body and support members are formed in an integrated manner.

Figure 4:
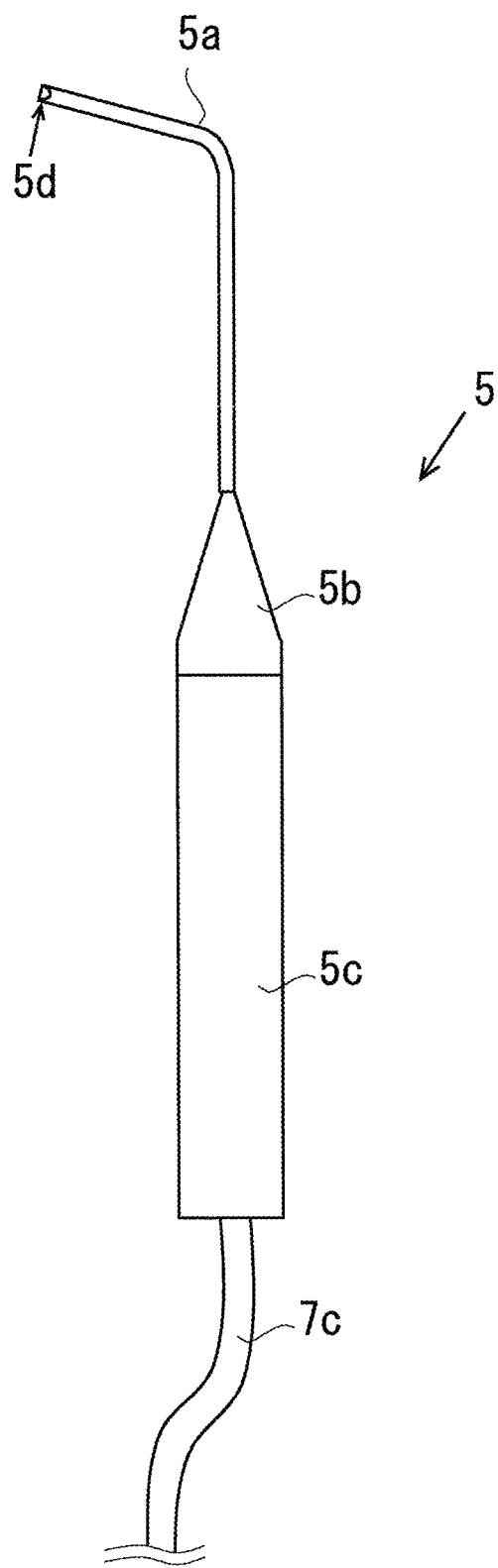
FIG. 4 is a diagram schematically illustrating a configuration of an irrigating solution infusion apparatus according to one embodiment.

FIG. 4 is a schematic view illustrating a configuration of the irrigating solution infusion apparatus 5. As illustrated in FIG. 4, the irrigating solution infusion apparatus 5 includes an irrigating solution infusion needle 5a, nozzle 5b and a grip member 5c. In addition, a tube 7c is connected with the irrigating solution infusion apparatus 5. The irrigating solution infusion needle 5a and the nozzle 5b are configured as a unit, and the nozzle 5b is detachably connected with the grip member 5c. Therefore, since the nozzle 5b is configured to be commonly used among different types of irrigating solution infusion needles, the irrigating solution infusion needles can be changed with each other to apply for the irrigating solution infusion apparatus 5. Since the tip of the irrigating solution infusion needle is used for adjusting the position of the intraocular lens 8 inserted into an eyeball, it is preferable not to configure the irrigating solution infusion needle 5a to have a knife-shaped edge or a sharp edge for preventing the intraocular lens from being damaged.

The user grabs the grip member 5c to hold the irrigating solution infusion apparatus 5 and inserts the tip of the irrigating solution infusion needle 5a into the eyeball through a lip referred to as a side port of the incision formed in the cornea of a patient. And irrigating solution is delivered from the irrigating solution source 2 to the irrigating solution infusion apparatus 5 via the tube 7c according to the operations of the foot pedal 4 by the user. The irrigating solution delivered to the irrigating solution infusion apparatus 5 is infused into the eyeball from the port 5d provided for the tip of the irrigating solution infusion needle 5a.

Experiment results regarding the amount of irrigating solution which is delivered from the irrigating solution source 2 and infused from the irrigating solution infusion apparatus 5 are described below. In an experiment, a bottle filled with irrigating solution is used as the irrigating solution source 2, the bottle is arranged at a position higher than the irrigating solution infusion apparatus 5, and the user pedals the foot pedal 4 to the first position. As a result, the lower the position of the irrigating solution source 2 becomes, the smaller the amount of irrigating solution delivered from the port 5d of the irrigating solution infusion needle 5a becomes, that is the weaker the momentum of irrigating solution infused from the port 5d becomes. In addition, the smaller the opening area of the port 5d of the irrigating solution infusion needle 5a becomes, the smaller the amount of irrigating solution delivered from the port 5d of the irrigating solution infusion needle 5a becomes, that is the weaker the momentum of irrigating solution infused from the port 5d becomes. Specifically, when the irrigating solution source 2 is arranged at a position about 100 cm higher than the irrigating solution infusion apparatus 5 and the outer diameter of the irrigating solution infusion needle 5a is 27G (Gauge), that is 0.40 mm, irrigating solution is not infused continuously but is discontinuously infused like droplet. However, when outer diameter of the irrigating solution infusion needle 5a is a gauge equal to or lower than 26G, more preferably a gauge equal to or lower than 25G, irrigating solution is infused continuously from the port 5d. Therefore, it is desirable to arrange the position of the irrigating solution source 2 at a position higher than the irrigating solution infusion apparatus 5 and configure the opening area of the port of the irrigating solution infusion needle 5a relative to the position of the irrigating solution source 2.

Further, since the smaller the incision becomes, the smaller the damage of the eye tissues becomes and the earlier the recovery of the damaged tissues becomes, the user forms as small an incision as possible according to an apparatus inserted into the eyeball. Therefore, when the cross section (the outer diameter) of the irrigating solution infusion needle 5a as an irrigating solution providing unit is configured to be smaller than the cross section (the outer diameter) of the nozzle member 15 of the intraocular lens insertion apparatus 6, the side port through which the irrigating solution infusion apparatus 5 is inserted can be configured to be smaller than the incision through which the intraocular lens insertion apparatus 6 is inserted, and the damage of the eye tissues can be minimized. The outer diameter of a nozzle member of an intraocular lens insertion apparatus generally ranges from 1.5 mm to 3.0 mm. And the outer diameter of a nozzle member of a mainstream intraocular lens insertion apparatus is 2.0 mm and the cross section thereof is approximately 3 mm$^2$. On the other hand, the cross section of the irrigating solution infusion needle 5a with the outer diameter of 25G which is preferable for the above experiment is approximately 0.2 mm$^2$, which is meaningfully smaller than the cross section of the nozzle member of the intraocular lens insertion apparatus.

Although the irrigating solution infusion needle 5a can be used to adjust the position of the intraocular lens inserted into the eyeball, this may cause that the user inserts the irrigating solution infusion needle 5a deeply in the eyeball by mistake and the eye tissues such as the capsule of crystalline lens are damaged by the needle because the user handles the irrigating solution infusion apparatus 5 with one hand and it may be more difficult for the user to handle the needle with one hand than with both hands. Therefore, the irrigating solution infusion needle 5a can be configured to have an uneven surface at a position where the needle is not inserted beyond necessity such that the outer diameter on the side of the nozzle 5b is larger than the outer diameter on the side of the port 5d. Alternatively, the irrigating solution infusion needle 5a can be configured to have a collar member such as a sleeve and an O-ring. The collar member can be integrally formed with the irrigating solution infusion needle 5a or can be attached to the irrigating solution infusion needle 5a afterward. It is preferable that the collar member is formed of an elastic material. Alternatively, irrigating solution infusion needle 5a can be configured to have a mark for indicating the amount of insertion of the needle. In addition, when the intraocular lens insertion apparatus 6 or the irrigating solution infusion apparatus 5 is inserted through the incision and the space between the intraocular lens insertion apparatus 6 or the irrigating solution infusion apparatus 5 and the incision is wide, irrigating solution may drain. However, the uneven surface or the collar member provided for the irrigating solution infusion needle 5a caps the incision to prevent the irrigating solution from draining.

Next, a surgery using the intraocular lens insertion system 1 according to the present embodiment is described below. It is assumed here that the washing within the eyeball has been performed by crushing and removing the human crystalline lens by phacoemulsification and aspiration and removing unnecessary cortex from the capsule of crystalline lens etc. In addition, it also assumed here that a side port through which the irrigating solution infusion apparatus 5 is inserted into the eyeball and an incision through which the intraocular lens insertion apparatus 6 is inserted into the eyeball have been produced. However, an incision through which both the irrigating solution infusion apparatus 5 and the intraocular lens insertion apparatus 6 are inserted into the eyeball can be produced such that only one incision is produced for the surgery.

The user inserts the tip of the irrigating solution infusion needle 5a of the irrigating solution infusion apparatus 5 into the eyeball through the side port. As a result, the port 5d is also inserted into the eyeball. Next, the user pedals the foot pedal 4 to the first position. As a result, the delivery of irrigating solution from the irrigating solution source 2 to the irrigating solution infusion apparatus 5 is started by the foot pedal 4. The irrigating solution delivered to the irrigating solution infusion apparatus 5 is infused from the port 5d into the eyeball. As a result, the capsule of crystalline lens is inflated by the irrigating solution delivered into the eyeball. When the user pedals the foot pedal 4 to maintain the foot pedal 4 at the first position, the infusion of irrigating solution delivered by the irrigating solution infusion apparatus 5 into the eyeball is maintained. As a result, the inflation of the capsule of crystalline lens can also be maintained.

Next, the user moves the intraocular lens 8. Specifically, the user wets the inner wall of the intraocular lens insertion apparatus 6 which provides a path for the intraocular lens in advance before the delivery of fluid from the driving source 3 to the intraocular lens insertion apparatus 6 is started. This lubricates the inner wall of the intraocular lens insertion apparatus 6. The user pedals the foot pedal 4 to the first position, and further pedals the foot pedal to the second position before the user inserts the distal end member 10a of the intraocular lens insertion apparatus 6 into the eyeball. As a result, fluid is delivered from the driving source 3 to the intraocular lens insertion apparatus 6, and the intraocular lens 8 is pushed to the nozzle member 15 by the plunger 30 of the intraocular lens insertion apparatus 6. And then, the user allows the foot pedals 4 to move back to the first position, and the user inserts the distal end member 10a of the intraocular lens insertion apparatus 6 into the eyeball through the incision produced for the cornea of the eyeball. After the user checks that the position of the distal end member 10a of the intraocular lens insertion apparatus 6 inserted into the eyeball is appropriate, the user pedals the foot pedal 4 to the second position.

As a result, the delivery of fluid from the driving source 3 to the intraocular lens insertion apparatus 6 is started by the foot pedal 4. When the foot pedal 4 is pedaled to the second position in the present embodiment, the foot pedal 4 maintains the delivery of irrigating solution from the irrigating solution source 2 to the irrigating solution infusion apparatus 5. Therefore, the infusion of irrigating solution into the eyeball from the irrigating solution infusion apparatus 5 is continued. When fluid is delivered from the driving source 3 to the intraocular lens insertion apparatus 6, the insertion operation of the intraocular lens 8 by the intraocular lens insertion apparatus 6 is started.

FIG. 5 illustrates an example of the relation between the position of the plunger 30 and the position of the piston 20c of the push assisting apparatus 20 when the intraocular lens 8 is inserted into the eyeball by the intraocular lens insertion apparatus 6. When the user uses the plunger 30 to move the intraocular lens 8 housed in the intraocular lens insertion apparatus 6, the user pedals the foot pedal 4 to deliver fluid with a constant flow from the driving source 3 to the first area 20f via the tube 7d and the fluid delivery member 20d. As a result, the first area 20f is filled with the fluid.

When the fluid is delivered to the first area 20f, the pressure applied to the piston 20c by the fluid increases. And when the force for pushing the piston 20c by the fluid becomes larger than the maximum static frictional force of the piston 20c, the piston 20c moves forward, that is to the side of the nozzle body 10. And the piston 20c comes into contact with the push plate member 33 of the plunger 30.

When fluid is further delivered to the first area 20f, the piston 20c further moves to the side of the nozzle body 10, and pushes the plunger 30 to move to the side of the nozzle body 10 accordingly. As a result, the intraocular lens 8 can be moved to the side of the distal end member 10a of the nozzle body 10. Next, the function of the through-hole 20b is described below. As illustrated in FIG. 5B, when the piston 20c moves beyond the hole 20b, the fluid delivered to the first area 20f drains from the hole 20b.

When the user unintentionally pedals the foot pedal 4 to deliver fluid from the driving source 3 to the intraocular lens insertion apparatus 6, it can be assumed that the hole 20b is not blocked by the user's hand etc. In this case, even when fluid is delivered to the first area 20f after the piston 20c moves to the position as illustrated in FIG. 5B, the delivered fluid drains from the hole 20b to the outside of the tube member 20a. As a result, the piston 20c is not pushed by the fluid thereafter and stops at the position as illustrated in FIG. 5B. Since the hole 20b is provided for the intraocular lens push assisting apparatus 20 as described above, this configuration can prevent an event in which the piston 20c continues to push the plunger 30 to the side of the distal end member 10a of the nozzle body 10 even when fluid is delivered to the first area 20f by mistake, and prevent, as a result, an event in which the intraocular lens 8 is ejected from the distal end member 10a of the nozzle body 10 despite the user's intentions.

On the other hand, when the user intentionally pedals the foot pedal 4 to deliver fluid from the driving source 3 to the intraocular lens insertion apparatus 6, it can be assumed that the hole 20b is blocked by the user's hand etc. In this case, when fluid is continued to be delivered to the first area 20f after the piston 20c moves to the position as illustrated in FIG. 5B, the delivered fluid does not drain from the hole 20b to the outside of the tube member 20a. As a result, when the delivery of fluid to the first area 20f is maintained, the piston 20c is continuously pushed by fluid and moves to the side of the distal end member 10a of the nozzle body beyond the position as illustrated in FIG. 5B. And the plunger 30 is pushed and moved by the piston 20c to move the intraocular lens 8 further to the side of the distal end member 10a of the nozzle body 10.

When the piston 20c moves further to the side of the distal end member 10a of the nozzle body beyond the position as illustrated in FIG. 5B, the user can releases the user's hand from the hole 20b to allow the delivered fluid to drain from the hole 20b and stop the movement of the piston 20c. Therefore, the user can control the movement of the piston 20c by blocking the hole 20b by the user's hand and releasing the user's hand from the hole 20b. With this configuration, the user does not need to handle the plunger by the user's finger and can concentrate on tasks and treatments including the adjustment of the position of the nozzle body 10 in relative to the incision.

In addition, when the foot pedal 4 is pedaled to deliver fluid with a constant flow into the intraocular lens push assisting apparatus 20, the piston 20c and furthermore the plunger 30 can be moved at a constant speed. Therefore, the intraocular lens insertion system 1 employing the intraocular lens insertion apparatus 6 according to the present embodiment achieves a more stable ejection of the intraocular lens into the eyeball than a conventional intraocular lens insertion system. In addition, since a more stable movement of the intraocular lens can also be achieved, the stress to the incision produced for the cornea of the eyeball can be reduced.

When the intraocular lens 8 is ejected from the intraocular lens insertion apparatus 6, the user adjusts the position of the foot pedal 4 to stop the delivery of fluid to the intraocular lens insertion apparatus 6. When the user arranges the intraocular lens 8 at an appropriate position, the user extracts the distal end member 10a of the intraocular lens insertion apparatus 6 from the incision. In addition, after the user pedals the foot pedal 4 to infuse a desired amount of irrigating solution into the eyeball from the irrigating solution infusion apparatus 5 for adjusting the intraocular pressure and to stop the delivery of fluid to the irrigating solution infusion apparatus 5, and then the user extracts the irrigating solution infusion needle 5a from the side port.

When the intraocular lens insertion system according to the present embodiment is used, the path for delivering irrigating solution into the eyeball and the path for delivering the intraocular lens into the eyeball can differ from each other. Therefore, the present embodiment can resolve a concern related to conventional intraocular lens insertion apparatus that lubricant applied to the inside of the intraocular lens insertion apparatus may be removed by irrigating solution delivered into the eyeball via the intraocular lens insertion apparatus. In addition, since the user can perform the infusion of irrigating solution into the eyeball and the insertion of the intraocular lens as a series of operations with just the adjustment of the pedaling of the foot pedal 4, it can be expected to achieve a more smooth operation according to the present embodiment.

Although the intraocular lens insertion system 1 is described above, the basic functions of the intraocular lens insertion system 101 is similar to those of the intraocular lens insertion system 1 except that the foot pedal 4 is an electric device and independently controls the irrigating solution source 102 and the driving source 103 to achieve controls of the delivery of irrigating solution from the irrigating solution source 102 to the irrigating solution infusion apparatus 105 and the delivery of driving force from the driving source 103 to the intraocular lens insertion apparatus 106. Further, the configurations of the intraocular lens insertion systems etc. according to the present invention are not limited to those as described above and several variations may be made to the embodiment described herein within the technical scope of the above embodiment.

FIGS. 6 and 7 exemplify modifications of the intraocular lens insertion system according to the above embodiment. In the description made hereinafter, respective constitutional elements corresponding to the constitutional elements of the above-mentioned embodiment are given the same symbols, and the detailed descriptions of the constitutional elements are omitted. FIGS. 6 and 7 illustrate configurations of an intraocular lens insertion apparatus 200 including a pressure control valve 210 and an intraocular lens insertion apparatus 300 including a pressure control valve 310, respectively. The pressure control valves 210, 310 are configured to let the delivered fluid out to the atmosphere when a pressure larger than a specific pressure is applied to the valves. A check valve is an example of the pressure control valve. In the variation example as illustrated in FIGS. 6A and 6B, the second area 20g is not enclosed space, the fluid delivery member 20d is connected with a three-way connector 220, and the tube 7d and the pressure control valve 210 are connected with an opening member 220a and an opening member 220b of the three-way connector 220, respectively. With this configuration, the difference between the pressure in the first area 20f and the pressure in the second area 20g can be adjusted to achieve a slow movement of the piston 20c and therefore the possibility of an accidental lens ejection that an intraocular lens shoots from the tip of an intraocular lens insertion apparatus and eye tissues of the eyeball into which the intraocular lens is inserted may be damaged by the shot intraocular lens can be reduced.

Additionally, in a variation example illustrated in FIGS. 7A, 7B and 7C, a hold member 18 of an intraocular lens insertion apparatus 300 is configured to connect with the tube member 20a of the intraocular lens push assisting apparatus 20 in a screw mating manner. FIG. 7C illustrates a partial cross section of the intraocular lens insertion apparatus 300 dissected by the A-A line in FIG. 7B. The hold member 18 includes a cylindrical member 18a which is in contact with the outer surface of the tube member 20a. A thread groove 18b is formed on the inner surface of the cylindrical member 18a. In addition, a thread groove 20j is formed on the outer surface of the tube member 20a in an area in which the outer surface of the tube member 20a comes into contact with the inner surface of the hold member 18. With this configuration, the cylindrical member 18a and tube member 20a are fixed to each other in the screw mating manner. Further, a concave member 20k is formed on the distal end surface of the tube member 20a and an O-ring 20m is attached into the concave member 20k. When the cylindrical member 18a and the tube member 20a are fixed to each other in the screw mating manner, the O-ring 20m comes into contact with the hold member 18. As a result, the possibility that fluid filled in the second area 20g of the tube member 20a may drain from between the cylindrical member 18a and the tube member 20a can be reduced.

Additionally, as illustrated in FIG. 7B, the pressure control valve 310 is attached to the tube member 20a. When the pressure from the fluid delivered to the second area 20g becomes larger than a predetermined pressure, the pressure control valve 310 lets the fluid in the second area 20g drain to the outside of the tube member 20a. With this configuration, the difference between the pressure in the first area 20f and the pressure in the second area 20g can be adjusted to achieve a slow movement of the piston 20c and therefore the possibility of an accidental lens ejection that an intraocular lens shoots from the tip of an intraocular lens insertion apparatus and eye tissues of the eyeball into which the intraocular lens is inserted may be damaged by the shot intraocular lens can be reduced.

Regarding a further variation example of the above embodiment, when the user pedals the foot pedal 4 to a position deeper than the second position in the above embodiment, the delivery of irrigating solution from the irrigating solution source 2 to the irrigating solution infusion apparatus 5 and the delivery of fluid from the driving source 3 to the intraocular lens insertion apparatus 6 are performed. However, the foot pedal 4 in this variation example can be configured to stop the delivery of irrigating solution from the irrigating solution source 2 to the irrigating solution infusion apparatus 5 and continue the delivery of fluid from the driving source 3 to the intraocular lens insertion apparatus 6 when the user pedals the foot pedal 4 to a position deeper than the second position. Alternatively, the foot pedal 4 in this variation example can be configured to stop the delivery of fluid from the driving source 3 to the intraocular lens insertion apparatus 6 and continue the delivery of irrigating solution from the irrigating solution source 2 to the irrigating solution infusion apparatus 5 when the user pedals the foot pedal 4 to a position deeper than the second position. Alternatively, the foot pedal 4 in this variation example can be configured to continue the delivery of irrigating solution from the irrigating solution source 2 to the irrigating solution infusion apparatus 5 while the fluid is being delivered from the driving source 3 to the intraocular lens insertion apparatus 6. Alternatively, the foot pedal 4 in this variation example can be configured to increase the amount of irrigating solution and/or fluid according to the position of the foot pedal 4 pedaled by the user. Alternatively, the foot pedal 4 in this variation example can be configured to have a function of inverting the delivery of fluid from the driving source 3 to the intraocular lens insertion apparatus 6, that is aspirating the delivered fluid.

A further alternative configuration may employ a configuration that the start and the stop of the delivery of irrigating solution from the irrigating solution source 2 to the irrigating solution infusion apparatus 5 and the start and the stop of the delivery of fluid from the driving source 3 to the intraocular lens insertion apparatus 6 are respectively controlled according to the number of operations of the foot pedal 4 instead of the configuration that the operations of the irrigating solution source 2 and the driving source 3 are controlled according to the amount of pedaling of the foot pedal 4.

In addition, a switch can be provided for the irrigating solution infusion apparatus 5 or the intraocular lens insertion apparatus 6 in place of the foot pedal 4, and the user can use the switch by a hand for controlling the operations of the irrigating solution source 2 and the driving source 3 while the user is handling the irrigating solution infusion apparatus 5 or the intraocular lens insertion apparatus 6. Alternatively, a switch can be provided for at least one of the irrigating solution infusion apparatus 5 and the intraocular lens insertion apparatus 6 in addition to the foot pedal 4, and the user can use the foot pedal 4 as a main control means for controlling the delivery of irrigating solution from the irrigating solution source 2 to the irrigating solution infusion apparatus 5 and the delivery of fluid from the driving source 3 to the intraocular lens insertion apparatus 6 and can use the switch provided for the irrigating solution infusion apparatus 5 and/or the intraocular lens insertion apparatus 6 as a sub control means for controlling the start and the stop of the delivery of irrigating solution into the eyeball and controlling the start and the stop of the insertion of the intraocular lens which is achieved by providing the driving force to the intraocular lens insertion apparatus 6. With this configuration, a refine control of each member in the intraocular lens insertion system can be achieved. It is noted that the through-hole 20b provided for the tube member 20a as described above also achieve an effect similar to the effect achieved by the switch provided for the intraocular lens insertion apparatus 6. Although the above descriptions are provided on the assumption that the driving force delivered from the driving source 3 is fluid, irrigating solution can be used as the driving force delivered from the driving source 3. In this case, the irrigating solution source 2 and the driving source 3 can be configured as a common unit.

It is possible that the user pedals the foot pedal 4 by mistake to a position deeper than a position that the user intends and the above controls are switched to start the movement of the intraocular lens despite the user's intentions. With the aim of preventing such an event, a configuration that a position of the foot pedal at which the user recognizes the switching of the controls and a position of the foot pedal at which the controls of the apparatuses are actually switched are temporally or spatially shifted from each other can be employed. With this configuration, even when the user pedals the foot pedal 4 by mistake to the position at which the user recognizes the switching of the controls, allowance to the position at which the controls are actually switched can be provided. As a result, the user adjusts the position of the foot pedal 4 back to the position at which the user intends.

Moreover, a motor can be provided for the intraocular lens insertion apparatus 6 and electric power can be used as the driving force delivered from the driving source 3 to electrically achieve the reciprocation of the plunger 30 inserted into the nozzle body 10. In this case, the tubes 7b, 7d are configured to have a function of transmitting electric signals. In addition, not only a wired connection but also a wireless connection can be employed for the electric connection of the tube which has the function of transmitting electric signals.

REFERENCE SIGNS LIST 1, 101 intraocular lens insertion system
2, 102 irrigating solution source
3, 103 driving source
4, 104 foot pedal
5, 105 irrigating solution infusion apparatus
6, 106 intraocular lens insertion apparatus
7a, 7b, 7c, 7d, 7e, 7f, 7g, 7h tube
8 intraocular lens

What is claimed is:

1. An intraocular lens insertion system comprising:
an intraocular lens insertion apparatus configured to use a predetermined driving force to move an intraocular lens and insert the intraocular lens into an eyeball;
an irrigating solution infusion apparatus configured to directly infuse irrigating solution into the eyeball;
a driving source configured to deliver the predetermined driving force to the intraocular lens insertion apparatus;
an irrigating solution source configured to deliver the irrigating solution to the irrigating solution infusion apparatus; and
a switching unit configured to switch in a multistage manner a control of a delivery of the irrigating solution from the irrigating solution source to the irrigating solution infusion apparatus and a control of a delivery of the predetermined driving force from the driving source to the intraocular lens insertion apparatus,
wherein a cross section of an irrigating solution providing unit of the irrigating solution infusion apparatus is smaller than a cross section of a nozzle member of the intraocular lens insertion apparatus.

2. The intraocular lens insertion system according to claim 1, wherein the switching unit is configured to switch in the multistage manner the control of the delivery of the irrigating solution from the irrigating solution source to the irrigating solution infusion apparatus and the control of a combination of the control of the delivery of the irrigating solution from the irrigating solution source to the irrigating solution infusion apparatus and the control of the delivery of the predetermined driving force from the driving source to the intraocular lens insertion apparatus.

3. The intraocular lens insertion system according to claim 1, wherein the switching unit is configured to deliver, at a first stage of an operation of the switching unit, the irrigating solution from the irrigating solution source to the irrigating solution infusion apparatus, and to deliver, at a second stage of the operation of the switching unit, the predetermined driving force from the driving source to the intraocular lens insertion apparatus while delivering the irrigating solution from the irrigating solution source to the irrigating solution infusion apparatus.

4. The intraocular lens insertion system according to claim 1, wherein the switching unit is a foot pedal.

5. The intraocular lens insertion system according to claim 4, further comprising:
a control unit configured to control the delivery of the irrigating solution to the irrigating solution infusion apparatus according to an operation of the foot pedal.

6. The intraocular lens insertion system according to claim 4, further comprising:
a control unit configured to control the delivery of the predetermined driving force to the intraocular lens insertion apparatus according to an operation of the foot pedal.

7. The intraocular lens insertion system according to claim 1, wherein a cross section of an irrigating solution providing unit of the irrigating solution infusion apparatus is smaller than a cross section of a nozzle member of the intraocular lens insertion apparatus.

8. The intraocular lens insertion system according to claim 1, wherein an inner wall forming a path on which the intraocular lens moves in the intraocular lens insertion apparatus is wet in advance before the delivery of the driving force from the driving source to the intraocular lens insertion apparatus is started.

9. An intraocular lens insertion apparatus configured to be used for the intraocular lens insertion system according to claim 1.

10. The intraocular lens insertion apparatus according to claim 9, wherein
a nozzle body is provided for a tip of the intraocular lens insertion apparatus,
the intraocular lens is moved in the nozzle body by the driving force, and
when the intraocular lens insertion apparatus is placed horizontally, a height of a distal end member of the nozzle body is equal to or more than 10 mm.

11. The intraocular lens insertion apparatus according to claim 9, wherein the intraocular lens is housed in advance in an intraocular lens housing unit of the intraocular lens insertion apparatus.

12. A tube configured to be used for the intraocular lens insertion system according to claim 1, wherein the tube is configured to connect the switching unit with at least one of the intraocular lens insertion apparatus, the irrigating solution infusion apparatus, the driving source and the irrigating solution source.

* * * * *